(12) United States Patent
Coppolino

(10) Patent No.: US 7,009,067 B2
(45) Date of Patent: Mar. 7, 2006

(54) HEXA-CITRATED PHYTATE AND PROCESS OF PREPARATION THEREOF

(75) Inventor: Carl Coppolino, Alpharetta, GA (US)

(73) Assignee: IP-6 Research, Inc., Baltimore, MD (US)

( * ) Notice: Subject to any disclaimer, the term of this patent is extended or adjusted under 35 U.S.C. 154(b) by 23 days.

(21) Appl. No.: 10/894,919

(22) Filed: Jul. 19, 2004

(65) Prior Publication Data

US 2005/0020543 A1    Jan. 27, 2005

Related U.S. Application Data

(60) Provisional application No. 60/488,786, filed on Jul. 21, 2003.

(51) Int. Cl.
*C07F 9/02* (2006.01)
*C07F 9/06* (2006.01)

(52) U.S. Cl. .......................... 558/70; 558/87; 558/129
(58) Field of Classification Search .................. 558/70, 558/87, 129
See application file for complete search history.

(56) References Cited

U.S. PATENT DOCUMENTS

| 5,876,997 | A | * | 3/1999 | Kretz | 435/196 |
| 6,114,387 | A | * | 9/2000 | Cutler | 514/562 |
| 6,183,740 | B1 | * | 2/2001 | Short et al. | 424/94.6 |
| 6,403,129 | B1 | * | 6/2002 | Clark et al. | 426/72 |

* cited by examiner

*Primary Examiner*—Golam M. M. Shameem
(74) *Attorney, Agent, or Firm*—Edwin P. Tarver; Patel & Alumit, P.C.

(57) ABSTRACT

The present invention relates to a new chemical compound known as hexa-citrated phytate and a method of production thereof. The new chemical compound has six citrate molecules attached at the hydroxyl group of a citric acid to phosphates of a phytate molecule. This new chemical compound is a very effective oral chelator maintaining metals and metalloids in the saline solution of blood. The new chemical compound is also very effective in dissolving artery plaque, as well as copper, zinc and iron.

8 Claims, No Drawings

HEXA-CITRATED PHYTATE AND PROCESS OF PREPARATION THEREOF

CROSS-REFERENCE TO RELATED APPLICATIONS

U.S. Provisional Application No. 60/488,786 (Filing Date: Jul. 21, 2003)

FEDERALLY SPONSORED RESEARCH

Not Applicable

SEQUENCE LISTING OR PROGRAM

Not Applicable

BACKGROUND OF THE INVENTION

1. Field of Invention

This invention relates to a new multiple ion chelator and method of production thereof. The new compound has six citrate molecules attached at the hydroxyl group of citric acid to the phosphates of a phytate molecule. Due to its rapid dissolution constant and enhanced chelating capacity, the new compound at very low concentrations is able to serve as an oral chelator that effectively dissolves artery plaque and removes excess copper, zinc, and iron deposits in the brain tissue to treat age-related degenerative disorders, such as Alzheimer's disease.

2. Prior Art

Chelators are small molecules that bind very tightly to metal ions. Some chelators are simple molecules that are easily manufactured (e.g., ethylenediaminetetraacetic acid). Others are complex proteins made by living organisms (e.g., transferrin). The key property shared by all chelators is that the metal ion bound to the chelator is chemically inert. Consequently, one of the important roles of chelators is to detoxify metal ions and prevent poisoning. For instance, Ethylendiaminetetraacetic acid (EDTA) is used to treat patients with extreme, life-threatening hypocalcaemia, while the iron chelator, desferrioxamine, is used to remove excess iron that accumulates with chronic blood transfusions. Although many different types of chelators exist, only a few are clinically useful since most have dangerous side effects. EDTA has long been thought of as a significant chelating agent. However, there has been known toxicological implications of EDTA when significant quantities and concentrations enter the vascular system. (See U.S. Pat. Nos. 5,114,974 and 6,114,387).

Meanwhile, phytic acid in the medical community has been known as an alternative to EDTA as a chelating agent. Phytic acid is a component of every plant seed and is found in a number of cereals and seeds. Although it is very soluble in water, alcohol (95% by volume) and acetone, it is only relatively soluble in aqueous propylene glycol and aqueous glycerol, and practically insoluble in ether, benzene and hexane. Aqueous solutions of phytic acid are intensely acidic: pH 0.9 at 66 grams/liter. Although phytic acid is a stable bioactive ingredient and free radical inhibitor with metal chelation abilities with strong buffering and antioxidant properties, it cannot be utilized as a proprietary flagship product.

BACKGROUND OF INVENTION—OBJECTS AND ADVANTAGES

In order to develop this new compound, experiments were conducted to determine, which conjugate would readily couple with phytic acid in order to reduce it to phytate or conversely determining which conjugate would be reduced by phytic acid to form a conjugate salt. Phytic acid (like EDTA) is a very strong chelator of bivalent and trivalent heavy metals such as mercury, cadmium, chromium, iron, lead and aluminum. Citric acid on the other hand is a very effective chelator for a monovalent ion, such as sodium, potassium and lithium. After consideration of many different nutritional supplements and bulk food commodities, it was discovered after countless experiments and computer modeling that the molecular structure of citric acid could be combined with phytic acid to form a new compound possessing most of the beneficial qualities of phytic acid and citric acid, which has been named hexa-citrated phytate. For example, hexa-citrated phytate is a very strong chelator of monovalent, bivalent and trivalent ions. Furthermore, hexa-citrated phytate circumvents the long suspected toxic and carcinogenic characteristics of EDTA.

Additionally, since citrate is combined with phytic acid at the carbon oxygen bond on each of the carbon atoms of the aromatic ring, the bonds between the oxygen atom of phytic acid and the citrate complex form very strong covalent bonds that help prevent instability of the molecule. Further, hexa-citrated phytate is very soluble despite its high molecular weight. Due to its numerous hydroxyl groups, hexa-citrated phytate is an extremely polar molecule that far exceeds the solubility and chelation properties of conventional chelators, such as inositol, phytic acid, and citric acid.

One primary use of hexa-citrated phytate is to act as an artery plaque dissolver. As many are aware, blood acts as a concentrated saline solution containing both dissolved and suspended solids that rapidly circulate through the arteries and the arterioles. Dissolved solids in the blood include nutrients absorbed from the colon and/or intestinal track. Suspended solids include platelets, red blood cells and white blood cells. Over time, some dissolved solids form solid precipitates that adhere to the inner walls of the circulatory system forming solid arterial plaque, which can lead to severe blockage in major blood vessels. However, due to the many chemical properties of hexa-citrated phytate, it is particularly successful in stripping plaque from arteries and arterioles. For example, hexa-citrated phytate is a highly soluble molecule with both hydrophobic and hydrophilic properties. Such a characteristic allows hexa-citrated phytate to remain dissolved in water due to its hydrophilic properties, while also allowing it to attach or adhere itself to solids that it comes into contact with as a result of its hydrophobic properties. As such, hexa-citrated phytate acts similarly to a surfactant allowing it to act as a removal agent of plaque from arteries and arterioles, while it rapidly flows through the cardiovascular system. Additionally, hexa-citrated phytate also has very powerful chelation characteristics that re-dissolve the precipitated solid. These re-dissolved materials are maintained in their soluble form until they are eventually excreted through the renal system.

Hexa-citrated phytate has several novel and significant differences from conventional chelators. First, the chemical compound has a rapid dissolution constant, which allows it to dissolve rapidly and readily. Due to this enhanced chelating capacity, the bonding of metals and metalloids with the conjugate product produces a soluble ionic product that maintains its soluble form in high concentrations in the saline solution of blood. As such, the chemical compound at very low concentrations has the ability to dissolve artery plaque for treatment of arteriolosclerosis, as well as the ability to remove copper, zinc, and iron deposits in the brain tissue for treatment of Alzheimer's disease and other age-related degenerative disorders.

Further objects and advantages will become apparent from a consideration of the ensuing description.

SUMMARY

In accordance with the present invention a new chemical compound known as hexa-citrated phytate and a method of production thereof is claimed. This new chemical compound is a very effective oral chelator maintaining metals and metalloids in the saline solution of blood. The new chemical compound is also very effective in dissolving artery plaque, as well as removing excess copper, zinc and iron in brain tissue.

DRAWINGS

Not applicable

DETAILED DESCRIPTION—PREFERRED EMBODIMENT

The present invention relates to a new chemical compound known as hexa-citrated phytate and a method of production thereof. The new chemical compound combines the citrate molecule converting the three carboxyl branches of citric acid into hydroxyl groups making it extremely soluble. In the compound, citric acid has been converted to a citrate with three hydroxyl groups per molecule. Each of the six carbons has an oxygen atom bound to citrate molecule and three hydroxyl groups are connected to each carbon atom of the citrate molecule. Due to this new compound, an extremely large polar molecule with numerous hydroxyl groups allows for high solubility and chelation properties. This new chemical compound with six citrate molecules attached at the hydroxyl group of a citric acid to phosphates of a phytate molecule has the following formula:

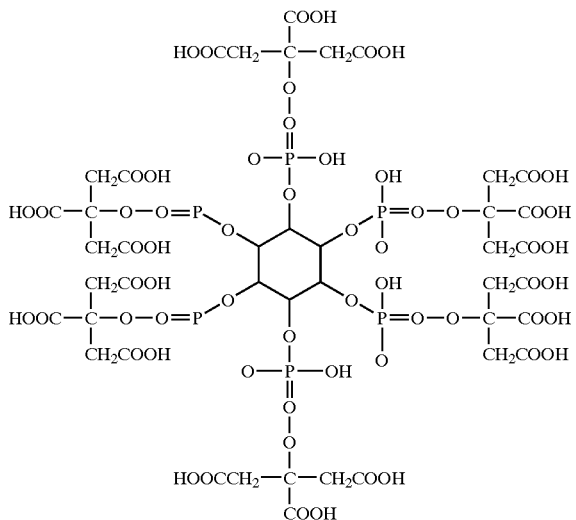

The new chemical compound is produced by: (1) slowly adding 0.33 kg of calcium carbonate in increments of 0.1 kg to 0.87 kg of phytic acid liquid; (2) heating and refluxing for one hour at 90 degrees Celsius; (3) separating the two solids by filtration; (4) gathering the white solid, which is calcium phytate; (5) dissolving 1 kg of calcium phytate into 2.0 liters of water; (6) heating to 89 degrees Celsius for 10–15 minutes until calcium phytate is dissolved in solution; (7) adding and stirring 0.90 kg of citric acid to solution until dissolved in solution; (8) removing heat source and setting solution in a refrigerated environment at a temperature of 5–10 degrees Celsius allowing crystallization for approximately 6 to 8 hours or until crystallization has ceased; (9) allowing the mixture to dry out at room temperature (75 degrees Celsius) until no liquid is visible, and (10) spreading crystals into a drying pan for approximately 24 hours at a temperature of no more than 40 degrees Celsius yielding approximately 1.2 kg of hexa-citrated phytate.

While the above description contains many specificities, these should not be construed as limitations on the scope of the invention, but as exemplifications of the presently preferred embodiments thereof. Many other ramifications and variations are possible within the teachings of the invention. Thus, the scope of the invention should be determined by the appended claims and their legal equivalents, and not by the examples given.

The invention claimed is:

1. A chemical compound represented by the following formula:

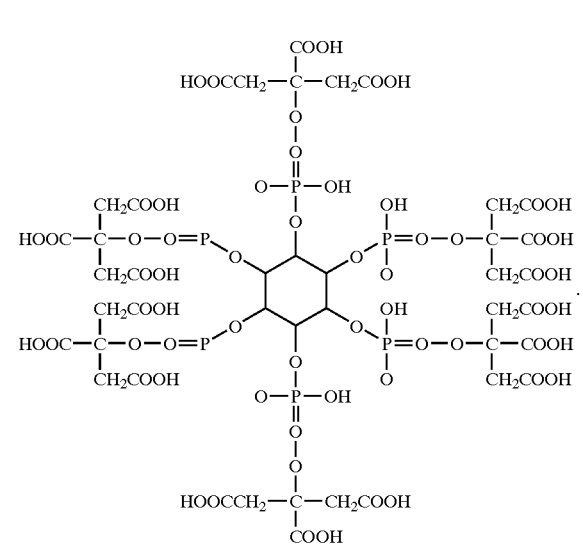

2. A method of production of hexa-citrated phytate according to the formula in the claim 1 comprising the steps of (1) slowly adding sufficient amount of calcium carbonate in increments to aqueous phytic acid at a ratio sufficient to allow all of reactants in solution to react; (2) heating and refluxing calcium carbonate and phytic acid solution for approximately one hour; (3) separating calcium phytate by filtration; (4) adding calcium phytate in sufficient amount of distilled water; (5) heating until calcium phytate is dissolved in solution; (6) adding and stirring citric acid to calcium phytate solution; (7) removing heat source and setting citric acid and calcium phytate solution in a refrigerated environment until crystallization has ceased; (8) allowing citric acid and calcium phytate solution to dry out at room temperature until no liquid is visible, and (9) spreading crystals into a drying pan.

3. The method of claim 2 wherein the amount of calcium carbonate is 0.33 kilograms; the amount of phytic acid is 0.87 kilograms; the amount of calcium phytate dissolved in water is 1 kilogram; the amount of citric acid is 0.9 kilograms; and the amount of water is 2.0 liters.

4. The method of claim 3 wherein the calcium carbonate is added to phytic acid in increments of 0.1 kilograms.

5. The method of claim 2 wherein the calcium carbonate and phytic acid solution is heated and refluxed at 90 degrees Celsius.

6. The method of claim 2 wherein the calcium phytate solution is heated at 89 degrees Celsius for 10 to 15 minutes.

7. The method of claim 2 wherein the refrigerated environment is between 5 to 10 degrees Celsius.

8. The method of claim 2 wherein crystals in the drying pan are allowed to dry for approximately 24 hours at no more than 40 degrees Celsius.

* * * * *